United States Patent [19]
Townsend et al.

[11] 3,962,211
[45] June 8, 1976

[54] 7-SUBSTITUTED NUCLEOSIDE COMPOUNDS

[75] Inventors: Leroy B. Townsend; Robert A. Earl, both of Salt Lake City, Utah

[73] Assignee: The University of Utah, Salt Lake City, Utah

[22] Filed: Jan. 13, 1975

[21] Appl. No.: 540,740

[52] U.S. Cl. .......................... 260/211.5 R; 424/180
[51] Int. Cl.² ............................................ C07H 19/16
[58] Field of Search .................... 260/211.5 R, 211.5

[56] References Cited
UNITED STATES PATENTS
3,535,207   10/1970   Shiro et al. .................... 260/211.5 R

*Primary Examiner*—Johnnie R. Brown

[57] ABSTRACT

Novel compounds of the formula

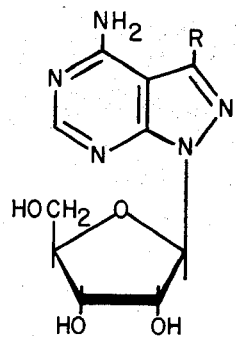

wherein R is selected from the group consisting of carboxamidine, carboxylic acid, carboxamide, methyl formimidate, thiocarboxamide, carboxamidoxime, carboxamidrazone, and cyano. The compounds have been demonstrated to be useful by having a degree of antimetabolic activity.

9 Claims, No Drawings

7-SUBSTITUTED NUCLEOSIDE COMPOUNDS

BACKGROUND AND FIELD OF THE INVENTION

This invention relates to chemical compounds and more particularly to 4-amino-3-substituted 1-beta-D-ribofuranosyl pyrazolo[3,4-d]pyrimidine nucleosides.

This invention was produced with the support of Drug Research and Development, National Cancer Institute, National Institute of Health, Department of Health, Education and Welfare, United States Government, under Research Contract NO1-CM-43806 and NO1-CM-23710.

BRIEF SUMMARY AND OBJECTS OF THE INVENTION

The present invention is directed to new compounds and more particularly to 4-amino-3-substituted 1-beta-D-ribofuranosyl pyrazolo[3,4-d]pyrimidines wherein the substituted group is selected from the group consisting of carboxamidine, carboxylic acid, carboxamide, methyl formimidate, thiocarboxamide, carboxamidoxime, carboxamidrazone, and cyano.

Preliminary investigations involving mice have shown that these new compounds are active antimetabolites.

It is therefore an object of this invention to provide certain new and useful pyrazolo[3,4-d]pyrimidine nucleosides.

DETAILED DESCRIPTION OF THE PREFERRED EMBODIMENTS

This invention relates to the synthesis of 4-amino-3-substituted 1-beta-D-ribofuranosyl pyrazolo[3,4-d]pyrimidines and offers a useful series of nucleosides for biological and chemotherapeutic evaluation as antimetabolites.

The preparation of these compounds includes the preparation of 4-acetamido-3-cyano-1-(2,3,5-tri-O-acetyl-beta-D-ribofuranosyl)pyrazolo[3,4-d]pyrimidine and thereafter preparing the 3-substituted derivatives of this compound which have been found to be 4-amino-3-substituted 1-beta-D-ribofuranosyl pyrazolo[3,4-d pyrimidines. These derivative compounds were experimentally determined to be active antimetabolites. These compounds result from the synthesis of 3,4-disubstituted derivations of 1-(beta-D-ribofuranosyl)pyrazolo[3,4-d]pyrimidine.

These compounds or 3-substituted derivatives are, respectively set forth as follows:

THE 3-METHYL FORMIMIDATE DERIVATIVE

The 3-methyl formimidate derivative has the following structure:

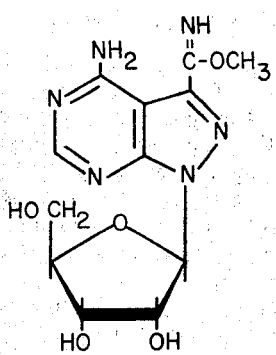

and is also known by its chemical name, methyl 4-amino-1-(beta-D-ribofuranosyl)pyrazolo[3,4-d]pyrimidine-3-formimidate monohydrate. For purposes of simplicity herein, the foregoing chemical name will be substituted, where possible, with the abbreviated designation, "3-methyl formimidate derivative".

THE 3-CARBOXAMIDINE DERIVATIVE

The 3-carboxamidine derivative has the following structure:

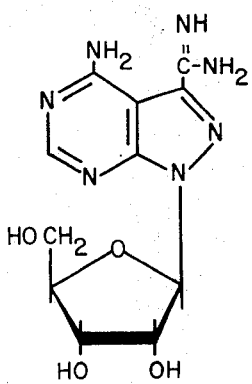

and is also known by its chemical name, 4-amino-1-(beta-D-ribofuranosyl)pyrazolo[3,4-d]pyrimidine-3-carboxamidine. For purposes of simplicity herein, the foregoing chemical name will be substituted, where possible, with the abbreviated designation, "3-carboxamidine derivative".

THE 3-THIOCARBOXAMIDE DERIVATIVE

The 3-thiocarboxamide derivative has the following structure:

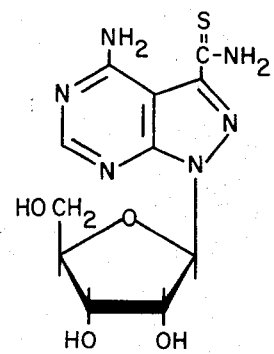

and is also known by its chemical name, 4-amino-1-(beta-D-ribofuranosyl)pyrazolo[3,4-d]pyrimidine-3-thiocarboxamide. For purposes of simplicity herein, the foregoing chemical name will be substituted, where possible, with the abbreviated designation, "3-thiocarboxamide derivative".

THE 3CARBOXAMIDE DERIVATIVE

The 3-carboxamide derivative has the following structure:

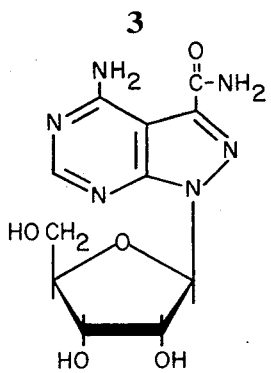

and is also known by its chemical name, 4-amino-1-(beta-D-ribofuranosyl)pyrazolo[3,4-d]pyrimidine-3-carboxamide. For purposes of simplicity herein, the foregoing chemical name will be substituted, where possible, with the abbreviated designation, "3-carboxamide derivative".

THE 3-CARBOXYLIC ACID DERIVATIVE

The 3-carboxylic acid derivative has the following structure:

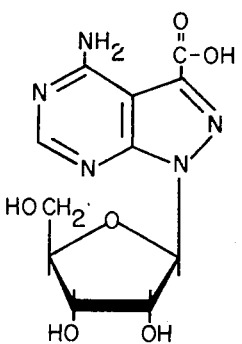

and is also known by its chemical name, 4-amino-1-(beta-D-ribofuranosyl)pyrazolo[3,4-d]pyrimidine-3-carboxylic acid. For purposes of simplicity herein, the foregoing chemical name will be substituted, where possible, with the abbreviated designation, "3-carboxylic acid derivative".

THE 3-CARBOXAMIDOXIME DERIVATIVE

The 3-carboxamidoxime derivative has the following structure:

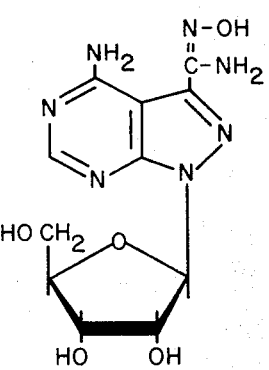

and is also known by its chemical name, 4-amino-1-(beta-D-ribofuranosyl)pyrazolo[3,4-d]pyrimidine-3-carboxamidoxime hemihydrate. For purposes of simplicity herein, the foregoing chemical name will be substituted, where possible, with the abbreviated designation "3-carboxamidoxime derivative".

THE 3-CARBOXAMIDRAZONE DERIVATIVE

The 3-carboxamidrazone derivative has the following structure:

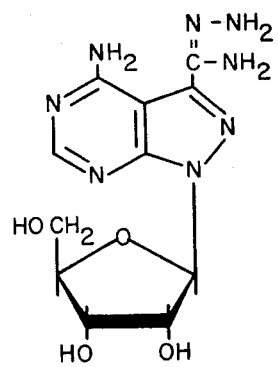

and is also known by its chemical name, 4-amino-1-(beta-D-ribofuranosyl)pyrazolo[3,4-d]pyrimidine-3-carboxamidrazone hemihydrate. For purposes of simplicity herein, the foregoing chemical name will be substituted, where possible, with the abbreviated designation "3-carboxamidrazone derivative".

THE 3-CYANO DERIVATIVE

The 3-cyano derivative has the following structure:

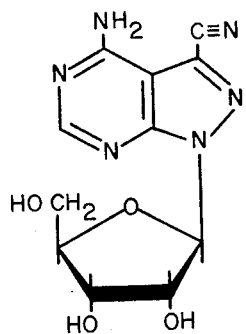

and is also known by its chemical name, 4-amino-3-cyano-1-(beta-D-ribofuranosyl)pyrazolo[3,4-d]pyrimidine monohydrate. For purposes of simplicity herein, the foregoing chemical name will be substituted, where possible, with the abbreviated designation "3-cyano derivative".

COMPOUND SCREENING

Screening of the novel and useful compounds of this invention was performed under the auspices of Drug Research and Development, National Cancer Institute, according to the protocols described in Instruction 14, of Cancer Chemotherapy Reports, 25, 3 (1962). The National Cancer Institute has adapted an evaluation criteria which defines any compound having a T/C of 125 or greater against Leukemia L 1210 as an active compound. T/C is a ratio of test animals (T) versus control animals (C) and is indicative of the increase in life span of the test animal over the control animal. For example, a T/C of 125 indicates that the test animal (T) had an increase of life span of 25% over the control animal (C).

In all of the tests conducted to evaluate the compounds of this invention, each mouse of a group of 5 mice (BDF1 Mice) was injected intraperitoneally with a tumor inducing agent, in this case leukemic cells. The group was then randomly divided into the test mice and the control mice. Only the test mice were treated with the particular test compound, otherwise, both test and control mice were given the same care. Dose injections of the test compound were administered on the basis of a predetermined number of milligrams per kilogram (mg/kg) animal body weight.

The results of the evaluation of each compound are reported after each example.

SYNTHESIS — GENERAL DISCUSSION

The novel 3-substituted derivative compounds of this invention were initially produced commencing with the condensation of 4-acetamido-3-cyanopyrazolo[3,4-d]pyrimidine with crystalline 2,3,5-tri-O-acetyl-beta-D-ribofuranosyl chloride to produce a good yield of a precursor material, 4-acetamido-3-cyano-1-(2,3,5-tri-O-acetyl-beta-D-ribofuranosyl)pyrazolo[3,4-d]pyrimidine, which on treatment with sodium methoxide in methanol provided a high yield of nucleoside which was subsequently established as the 3-methyl formimidate derivative.

The formimidate function of this 3-methyl formimidate derivative was found to be highly reactive. Additionally, the 3-methyl formimidate derivative was readily converted into the corresponding 3-carboxamidine derivative, the 3-carboxamidoxime derivative and the 3-carboxamidrazone derivative, when treated with the appropriate nucleophiles as will be set forth more fully with respect to appropriate examples herein.

In addition, treatment of the imidate, 3-methyl formimidate derivative, with sodium hydrogen sulfide gave a high yield of the 3-thiocarboxamide derivative which was then readily converted into the 3-cyano derivative.

Aqueous base transformed with 3-methyl formimidate derivative into the 3-carboxamide derivative while more vigorous basic hydrolysis provided the corresponding 3-carboxylic acid derivative, in nearly quantitative yield.

The site of ribosylation and the anomeric configuration for the nucleosides claimed herein was unequivocally established by the decarboxylation of the 3-carboxylic acid derivative in hot sulfolane to provide a high yield of the known compound, 4-amino-1-(beta-D-ribofuranosyl)pyrazolo[3,4-d]pyrimidine.

The reaction of 4-acetamido-3-cyanopyrazolo[3,4-d]pyrimidine with crystalline 2,3,5-tri-O-acetyl-beta-D-ribofuranosyl chloride in boiling nitromethane (utilizing potassium cyanide as the acid acceptor) provided a good yield (thin layer chromatography( of nucleoside material. Column chromatography provided a 56% yield of a chromatographically homogeneous syrup that was established as being 4-acetamido-3-cyano-1-(2,3,5-tri-O-acetyl-beta-D-ribofuranosyl)pyrazolo[3,4-d]pyrimidine. Treatment of 4-acetamido-3-cyano-1-(2,3,5-tri-O-acetyl-beta-D-ribofuranosyl)pyrazolo[3,4-d]pyrimidine with sodium methoxide in methanol resulted in the formation of crystalline nucleoside in 82% yield. This nucleoside was identified as the 3-methyl formimidate derivative. It is also found that the 3-methyl formimidate could be prepared directly (no chromatography), in yields of 50–60%, by treatment of crude 4-acetamido-3-cyano-(2,3,5-tri-O-acetyl-beta-D-ribofuranosyl)pyrazolo[3,4-d]pyrimidine with sodium methoxide in methanol.

It was also found that the reaction of 4-acetamido-3-cyano-1-(2,3,5-tri-O-acetyl-beta-D-ribofuranosyl) pyrazolo[3,4-d]pyrimidine with liquid ammonia at room temperature (40 hours) produced a good yield (76%) of the 3-carboxamidine derivative. A nearly identical yield (77%) of the crystalline amidine, the 3-carboxamidine derivative was also obtained on treatment of the 3-methyl formimidate with liquid ammonia under these conditions.

The imidate, the 3-methyl formimidate derivative can be considered as an activated form of 4-amino-3-cyano-1-(beta-D-ribofuranosyl(pyrazolo[3,4-d]pyrimidine which prompted the use of the 3-methyl formimidate derivative as an intermediate for the synthesis of the other desired 4-amino-3-substituted 1-beta-D-ribofuranosyl pyrazolo[3,4-d]pyrimidine nucleosides of this invention.

Both hydroxylamine and hydrazine hydrate reacted readily with the 3-methyl formimidate derivative to yield the corresponding 3-carboxamidoxime derivative (86%) and the 3-carboxamidrazone derivative (81%), respectively.

Sodium hydrosulfide in methanol reacted very rapidly (about 3 minutes) at room temperature with the 3-methyl formimidate derivative and the 3-thiocarboxamide derivative began to precipitate from solution. The 3-thiocarboxamide derivative was obtained initially as a low melting solid (m.p. 132°–135°C) which upon recrystallization from an ethanol-water mixture gave a higher melting form (m.p. 250.5°–251.5°C). A similar behavior was noted for the 3-carboxamidoxime derivative.

Treatment of the 3-thiocarboxamide derivative with mercuric chloride and triethylamine in dimethylformamide furnished the 3-cyano derivative.

A catalytic amount of sodium hydroxide in water effected a smooth conversion of the imidate, the 3-methyl formimidate derivative, into the more water insoluble 3-carboxamide derivative.

Treatment of the 3-carboxamide derivative with a slight excess of hot aqueous sodium hydroxide furnished a high yield (89%) of the 3-carboxylic acid derivative. The addition of an aquivalent amount of mineral acid furnished the 3-carboxylic acid derivative, in the form of a gelatinous precipitate which eventually crystallized. The 3-carboxylic acid derivative was surprisingly stable to heat (sinters at about 305°C).

The preparation of the novel compounds of this invention required the preparation of the intermediate compounds 4-acetamido-3-cyanopyrazolo[3,4-d]pyrimidine and 4-acetamido-3-cyano-1-(2,3,5-tri-O-acetyl-beta-D-ribofuranosyl)pyrazolo[3,4-d]pyrimidine.

EXAMPLE 1

Preparation of 4-Acetamido-3-cyanopyrazolo[3,4-d]pyrimidine

A suspension of dry (1 h/110°C 0.5— torr) 4-amino-3-cyanopyrazolo[3,4-d]pyrimidine (20 g.), in a mixture of acetic anhydride (100 ml.) and dry pyridine (100 ml., which had been stored over potassium hydroxide pellets) was vigorously stirred and brought to reflux temperature during 5 min. The mixture was stirred vigorously and heated at reflux temperature for a total of 35 minutes (solution occurs in about 20 minutes). The solution was then cooled to room temperature (ice-bath) and concentrated in vacuo to give a dark, pasty solid. (Unless otherwise noted, all concentrations were carried out in vacuo at 35°C.) Methanol (100 ml.) was added and the solution was allowed to stand (0.5 hr.) followed by another concentration in vacuo. The solid was triturated with a mixture of ice and water (60 g. total) for 15 min. and the solid was collected by filtration. The dark colored filter cake was washed with cold water (0°C) (2 × 20 ml.).

The moist solid was then dissolved in 850 ml. of boiling water, treated with a purified charcoal (3 g.) and filtered while hot. The filtrate was cooled to 0°C and the tan colored solid collected by filtration. The solid was then dissolved in the minimum amount of 1.25 N sodium hydroxide solution required to effect a solution (about 75 ml.), treated with purified charcoal (2 g.) and the filtered. The filtrate was cooled to 0°C and stirred while the solution was adjusted to pH 5 by the dropwise addition of acetic acid. The white precipitate was collected by filtration, washed with cold (0°C) water (2 × 15 ml.) and after drying in vacuo (25°C, 0.5 torr Hg) furnished 13.4 g. (53%) of 4-acetamido-3-cyanopyrazolo [3,4-d]pyrimidine (m.p. >360°C). A small sample was crystallized twice from water to give small white needles (m.p.>360°C).

Analysis: Calculated for $C_8H_8N_6O$: C, 47.40; H, 2.99; N, 41,58. Found: C, 47.38; H, 2.93; N, 41.49.

EXAMPLE 2

Preparation of 4-Acetamido-3-cyano-1-(2,3,5-tri-O-acetyl-beta-D-ribofuranosyl)pyrazolo[3,4-d]pyrimidine All operations, for this preparation were carried out in an efficient fume hood since copius amounts of hydrogen cyanide are evolved. 4-Acetamido-3-cyanopyrazolo[3,4-d]pyrimidine (10.4 g., 51.3 mmole), obtained from Example 1, and potassium cyanide (3.41 g., 52.3 mmole) were finely pulverized, dried separately (8 hr., 110°C/0.5 torr Hg) and then placed in a dry flask containing nitromethane (384 ml. dried over 4 A molecular sieves for 2 days). The mixture was heated to reflux temperature while stirring vigorously and then 14.8 g. (50.3 mmole) of crystalline 2,3,5-tri-O-acetyl-beta-D-ribofuranosyl chloride (m.p. 46°–50°C) was added in one portion. Vigorous stirring and heating was continued for 2 hours and the mixture was then concentrated in vacuo to a brown syrup which contained some suspended solid. The syrup was dissolved in 300 ml. of ethyl acetate and washed in succession with water (100 ml.), saturated sodium bicarbonate solution (4 × 50 ml.) and then a saturated sodium chloride solution (2 × 20 ml.). The solution was dried (anhydrous sodium sulfate) and then passed through a pad of silica gel (5 × 7 cm.). The pad of silica gel was washed with ethyl acetate (2 × 20 ml.) and the filtrates were then combined and concentrated in vacuo to yield a light brown foam (20 g.).

The foam was dissolved in chloroform (15 ml.) and applied to the top of a dry packed column (37 × 6.5 cm.) of silica gel (607 g.) and the column eluted with a mixture of chloroform -acetone - methanole (44:5:1) with 20 ml. fractions being collected. Fractions 10–34 contained the faster running component (pale yellow foam, 12.9 g., 56%), fractions 34–45 contained 3.4 g. of a mixture (mostly the faster running component) and fractions 46–50 contained 730 mg. of the slower moving component. Examination of the slowing moving component by proton magnetic resonance revealed that it was a mixture of two compounds and this material was not examined further. The faster moving, major component was assigned the structure 4-acetamido-3-cyano- 1-(2,3,5-tri-O-acetyl-beta-D-ribofuranosyl)pyrazolo[3,4-d]pyrimidine on the basis of ascertained physiochemical data.

EXAMPLE 3A

Preparation of the 3-Methyl Formimidate Derivative, Methyl 4-amino-1-(beta-D-ribofuranosyl)pyrazolo[3,4-d]pyrimidine-3-formimidate monohydrate Sodium metal (about 10 mg.) was dissolved in 50 ml. of dry methanol (distilled from calcium hydride) and then chromatographically homogeneous 4-acetamido-3-cyano-1-2,3,5-tri-O-acetyl-beta-D-ribofuranosyl)-pyrazolo[3,4-d]pyrimidine (as a dry foam, 3.89 g. obtained from Example 2) was added. Solution occurred immediately and in about 70 minutes the reaction was essentially complete. The reaction mixture was adjusted to a "pH" of 7 by the addition of small portions of Dowex 50, the trade name for a commercially available ion-exchange resin of the Dow Chemical Company, ($H_+$ form, prewashed with anhydrous methanol). The solution was then quickly filtered to remove the ion-exchange resin followed by concentration in vacuo.

Trituration of the residue with isopropanol (3 × 10 ml.) afforded a light yellow powder (2.44 g.) that was recrystallized from methanol to give 2.2 g. (82%) of the 3-methyl formimidate derivative as a pale yellow powder (m.p. about 127°–131°C). A sample was recrystallized once more (methanol - water) for analysis; shiny clusters, m.p. 132°C ( forms a highly viscous melt that bubbles at 145°C).

Analysis: Calculated for $C_{12}H_{10}N_6O_5 \cdot H_2O$: C, 42.1; H, 5.3; N, 24.55. Found: C, 42.1; H, 5.4; N, 24.7.

Alternately, the crude product (light brown foam) obtained during the preparation (Example 2) of 4-acetamido-3-cyano-1-(2,3,5-tri-O-acetyl-beta-D-ribofuranosyl)pyrazolo[3,4-d]pyrimidine (after passing the solution through a silica gel pad followed by evaporation) could be treated as above to give the product in over all yields (based on the amount of 4-acetamido-3-cyanopyrazolo [3,4-d]pyrimidine used in the reaction) of 50–60%.

EXAMPLE 3B

Utilizing the aforementioned protocol of Drug Research and Development, National Cancer Institute, separate sample groups of mice were selected. All mice in each sample group received an injection of leukemic cells intraperitoneally. One half of the mice were then randomly selected as control mice (C). The remaining mice served as the test mice (T) and each received preselected dosages of the particular 3-substituted derivative on the basis of milligrams per kilogram of animal body weight (mg/kg).

The increased life expectancy of the test mice (T), as measured from the deaths of the control mice (C), gave the T/C ratios following the value indicating the dose injection. Evaluation of the 3-methyl formimidate derivative obtained from Example 3A resulted in the following T/C values:

| Sample No. 1 | 400 mg/kg | 164 T/C |
| Sample No. 2 | 200 mg/kg | 153 T/C |
| Sample No. 3 | 100 mg/kg | 136 T/C |

EXAMPLE 4A

Preparation of the 3-Carboxamidine Derivative, 4-Amino-1-(beta-D-ribofuranosyl)pyrazolo[3,4-d]pyrimidine-3-carboxamidine.

Method 1

The 3-methyl formimidate derivative obtained from Example 3A (1.5 g.) was added to 10 ml. of liquid ammonia in a steel reaction vessel and the vessel was sealed and allowed to stand for 40 hours at room temperature. The ammonia was then allowed to evaporate and the residue suspended in 10 ml. of boiling water. Methanol was added to the boiling mixture until a clear solution had occurred and the solution was then concentrated to a volume of 10 ml. by heating. Crystallization was allowed to take place at room temperature. The solid was collected by filtration and washed with a small amount of cold (0°C) methanol to give 1.1 g. (77%) of the 3-carboxamidine derivative as small rosettes (m.p. 188°–190°C). A sample was recrystallized from methanol (needles, m.p. 189°–190°C).

Analysis: Calculated for $C_{11}H_{14}N_7O_4$: C, 42.7; H, 4.9; N, 31.7. Found: C, 42.7; H, 5.0; N, 31.6.

Method 2

Chromatographically homogeneous 4-acetamido-3-cyano-1-(2,3,5-tri-O-acetyl-beta-D-ribofuranosyl)-pyrazolo[3,4-d] pyrimidine (980 mg. of foam from Example 2) was treated as above. After evaporation of the ammonia, the solid residue was triturated with 13 ml. of ethanol-isopropanol (1:2) and then recrystallized from methanol-water to yield 500 mg. (76%) of the 3-carboxamidine derivative (in two crops, m.p. 188°–190°C).

EXAMPLE 4B

Evaluation of the 3-Carboxamidine Derivative

Following the same basic procedure as described in Example 3B, the 3-carboxamidine derivative obtained from Example 4A was evaluated with the following results:

| Sample No. 1 | 25.0 mg/kg | 196 T/C |
| Sample No. 2 | 42.0 mg/kg | 204 T/C |
| Sample No. 3 | 25.0 mg/kg | 201 T/C |
| Sample No. 4 | 15.0 mg/kg | 185 T/C |
| Sample No. 5 | 9.0 mg/kg | 159 T/C |

EXAMPLE 5A

Preparation of the 3-carboxamidoxime Derivative, 4-Amino-1-(beta-D-ribofuranosyl)pyrazolo[3,4-d]pyrimidine-3-carboxamidoxime hemihydrate.

The 3-methyl formimidate derivative obtained from Example 3A (1.5 g., 4.17 mmole) was dissolved in anhydrous methanol (25 ml.) at reflux temperature and 0.5 g. (15 mmole) of crystalline hydroxylamine added. Solution was almost complete in 0.5 hr. when a solid other than the 3-methyl formimidate derivative started to separate from solution. The suspension was heated at reflux temperature a total of 2 hr., cooled to 9°C, the solid collected by filtration and washed with cold (0°C) methanol (2 × 5 ml.). The solid (fine crystals) weighed 1.34 g. (m.p. 151°–152°C foams). Recrystallization from 1:1 methanol-water (40 ml.) gave the pure carboxamidoxime derivative, 1.21 g. (86%), (m.p. 242°–244°C, clear melt).

Analysis: Calculated for $C_{11}H_{15}N_7O_5 \cdot 0.5\ H_2O$: C, 39.55; H, 4.8; N, 29.3. Found: C, 39.8; H, 4.9; N, 29.2.

EXAMPLE 5B

Evaluation of the 3-Carboxamidoxime Derivative

Following the same basic procedure as described in Example 3B, the 3-carboxamidoxime derivative obtained from Example 5A was evaluated with the following results:

| Sample No. 1 | 50.0 mg/kg | 123 T/C |
| Sample No. 2 | 25.0 mg/kg | 185 T/C |
| Sample No. 3 | 12.5 mg/kg | 143 T/C |

EXAMPLE 6B

Preparation of the 3-Carboxamidrazone Derivative, 4-Amino-1-(beta-D-ribofuranosyl)pyrazolo[3,4-d pyrimidine-3-carboxamidrazone hemihydrate.

To a suspension of the 3-methyl formimidate derivative obtained from Example 3A (1.5 g., 4.16 mmole) in methanol (30 ml.) was added 2.5 ml. (42.5 mmole) of 85% hydrazine hydrate. The mixture was warmed to effect a clear solution and the solution was then allowed to stand at 25°C for 18 hours. The clusters of pale yellow needles that had formed were collected by filtration and washed with small amounts of methanol to yield 1.25 g. of the 3-carboxamidrazone derivative, (m.p. 218°–220°C). A second crop (100 mg., m.p. 208°–210°C) was obtained from the supernatent. The crystals were combined and recrystallized from water (10 ml.) to give 1.12 g. (81.2%) of the pure 3-carboxamidrazone derivative, m.p. 220°–221°C.

Analysis: Calculated for $C_{11}H_{16}N_6O_4 \cdot 0.5\ H_2O$: C, 39.6; H, 5.1; N, 33.6. Found: C, 39.8; H, 5.2; N, 33.75.

EXAMPLE 6B

Evaluation of teh 3Carboxamidrazone Derivative

Following the same basic procedure as described in Example 3B, the 3-carboxamidrazone derivative obtained from Example 6A was evaluated with the following results:

| Sample No. 1 | 200 mg/kg | 113 T/C |
| Sample No. 2 | 166 mg/kg | 131 T/C |
| Sample No. 3 | 100 mg/kg | 125 T/C |
| Sample No. 4 | 60.0 mg/kg | 116 T/C |

EXAMPLE 7A

Preparation of the 3-Thiocarboxamide Derivative, 4-Amino-1-(beta-D-ribofuranosyl)pyrazolo[3,4-d]pyrimidine-3-thiocarboxamide.

Sodium metal (140 mg., 6.4 mmole) was dissolved in 45 ml. of anhydrous methanol and then anhydrous hydrogen sulfide was passed through the solution with magnetic stirring for 5 minutes. The nucleoside, 3-methyl formimidate derivative obtained from Example 3A (2.3 g., 6.4 mmole) was added in one portion to the stirred solution of sodium hydrogen sulfide and in about 3 minutes a clear solution had occurred followed by the immediate appearance of a yellow solid. The mixture was stirred for 2 hours at 25°C, cooled to 0°C and the solid which had separated was then collected by filtration and washed with cold methanol (2 × 7 ml.). The solid (m.p. 132°–135°C, vigorous bubbling with no odor) was dissolved in 400 ml. of an ethanol - water mixture (1:1). The solution was concentrated to 200 ml. by heating and this was followed by cooling to room temperature. The solid which had separated from solution was collected (filtration) and washed in succession with cold ethanol (2 × 5 ml.) and then anhydrous ether (10 ml.). The 3-thiocarboxamide derivative appeared as a light yellow solid which weighed 1.69 g. (81.3%), (m.p. 250°–251.5°C, vigorous decomposition, unpleasant odor). A small sample was recrystallized from a methanol - water mixture (m.p. 252°–253°C, decomposes as above).

Analysis: Calculated for $C_{11}H_{14}N_6O_4S$: C, 40.5; H, 4.3; N, 25.6. Found: C, 40.6; H, 4.6; N, 25.4.

EXAMPLE 7B

Evaluation of the 3-Thiocarboxamide Derivative

Following the same basic procedure as described in Example 3B, the 3-thiocarboxamide derivative obtained from Example 7A was evaluated with the following results:

| | | |
|---|---|---|
| Sample No. 1 | 3.12 mg/kg | 129 T/C |
| Sample No. 2 | 1.56 mg/kg | 143 T/C |

EXAMPLE 8A

Preparation of the 3-Cyano Derivative, 4-Amino-3-cyano-1-(beta-D-ribofuranosyl)-pyrazolo[3,4-d]pyrimidine monohydrate.

Dry (0.5 torr Hg, 25°C, 1 hour) 3-thiocarboxamide derivative obtained from Example 7A (1 g., 3.06 mmole) was dissolved in 70 ml. of warm (50°C) dimethylformamide. Mercuric chloride (0.84 g., 3.10 mmole) and triethylamine (1 ml., 7.24 mmole) were added to the dimethylformamide solution and the mixture stirred at room temperature for 3 hours. The solution was then filtered through a diatomaceous earth filter aid to remove the black mercuric sulfide that had formed. The filter cake was washed with dry dimethylformamide (10 ml.) and the pale yellow filtrates were combined and concentrated in vacuo. The residue was triturated with cold (0°C) methanol (10 ml.) to give 800 mg. of pale yellow solid. The solid was suspended in 20 ml. of boiling methanol and then water was added dropwise to the hot suspension until solution had been effected. The solvent was removed by heating until crystallization started (final volume about 15 ml.). Rapid stirring and cooling to 0°C gave 580 mg. (61%) of the 3-cyano derivative as a white solid, (m.p. 235°–238°C, decomposes). Repetition of the above crystallization procedure, with the aid of purified charcoal, gave 500 mg. (42.6%) of pure 3-cyano derivative (m.p. 238°–240°C, sinters with preliminary darkening at 225°C).

Analysis: Calculated for $C_{11}H_{12}N_6O_4 \cdot H_2O$: C, 42.6; H, 4.5; N, 27.1. Found: C, 42.8; H, 4.8; N, 27.2.

EXAMPLE 8B

Evaluation of the 3-Cyano Derivative

Following the same basic procedure as described in Example 3B, the 3-cyano derivative obtained from Example 8A was evaluated with the following results:

| | | |
|---|---|---|
| Sample No. 1 | 100 mg/kg | 127 T/C |
| Sample No. 2 | 50 mg/kg | 114 T/C |
| Sample No. 3 | 25 mg/kg | 110 T/C |

EXAMPLE 9A

Preparation of the 3-Carboxamide Derivative, 4-Amino-1-(beta-D-ribofuranosyl)pyrazolo[3,4-d]pyrimidine-3-carboxamide.

The nucleoside 3-methyl formimidate derivative obtained from Example 3A (2 g., 5.57 mmole) was suspended in 30 ml. of water and 1.0 ml. of 1.25 N sodium hydroxide solution was then added. The mixture was stirred at room temperature for 18 hours and the finely suspended solid was then collected by filtration (after cooling to 0°C). The 3-carboxamide derivative was recovered as a white solid which was washed with cold (0°C water 2 × 10 ml.) and then dried in vacuo (25°C, 0.5 torr Hg) to yield 1.78 g. of the 3-carboxamide derivative (m.p. 262°–265°C). Recrystallization of this solid from water (230 ml. required) gave an analytically pure product, 1.43 g. (74.5%), (m.p. 270°–271°C, brown melt, bubbling).

Analysis: Calculated for $C_{11}H_{14}N_6O_5$: C, 42.6; H, 4.5; N, 27.1. Found: C, 42.6; H, 4.7; N, 27.1.

EXAMPLE 9B

Evaluation of the 3-Carboxamide Derivative

Following the same basic procedure as described in Example 3B, the 3-carboxamide derivative obtained from Example 9A was evaluated with the following results:

| | | |
|---|---|---|
| Sample No. 1 | 200 mg/kg | 236 T/C |
| Sample No. 2 | 100 mg/kg | 258 T/C |
| Sample No. 3 | 50.0 mg/kg | 236 T/C |

EXAMPLE 10

Preparation of the 3-Carboxylic Acid Derivative, 4-Amino-1-(beta-D-ribofuranosyl)pyrazolo[3,4-d]pyrimidine-3-carboxylic acid.

The 3-carboxamide derivative obtained from Example 9A (730 mb., 2.14 mmole) was dissolved in 10 ml. of water containing 2.0 ml. of 1.25 N sodium hydroxide solution. The solution was heated at reflux temperature for 18 hours (ammonia evolution ceased during this period of time). The clear solution was then acidified by the addition of 2.45 ml. of 1.02 N hydrochloric acid solution. A gelatinous precipitate formed immediately and after further stirring this turned into a white solid. The suspension was stirred at 0°C for 1 hour and the solid collected by filtration. The solid was washed with cold (0°C) water (2 × 5 ml.) and then dissolved in hot water (60 ml.). The temperature was allowed to drop slowly to 0°C as crystallization proceeded. The solid was collected by filtration to yield 590 mg. (89%) of white needles (m.p. 296°C, sinters with darkening at 240°C). A small sample was recrystallized from water to afford an analytical sample of the 3-carboxylic acid derivative (darkens at 245°C, sinters at 305°C, m.p. > 360°C).

Analysis: Calculated for $C_{11}H_{13}N_5O_6$: C, 42.45; H, 4.2; N, 22.5. Found: C, 42.4; H, 4.3; N, 22.4.

EXAMPLE 11

Substantiation of the Anomeric Configuration and Site of Ribosylation of the 4-Amino-3-substituted 1-beta-D-ribofuranosyl pyrazolo[3,4-d]pyrimidine Nucleosides of this Invention.

The following protocol was followed to produce the known compound, 4-amino-1-(beta-D-ribofuranosyl)-pyrazolo[3,4-d]pyrimidine and thereby more clearly demonstrate by the decarboxylation of the 3-carboxylic acid derivative that the site of ribosylation and the anomeric configuration are as set forth for the claimed compounds.

Powdered, dry 3-carboxylic acid derivative obtained from Example 10 (330.3 mg. 1.06 mmole) was suspended in 15 ml of freshly distilled sulfolane (Phillips Petroleum Co.). Dry nitrogen was passed through the suspension for 0.5 hr and the suspension of the 3-carboxylic acid derivative was then lowered into a preheated (213°C) Woods metal bath. A smooth evolution of carbon dioxide started [evolved carbon dioxide was passed through a rubber tube to an inverted, filled (water) graduated cylinder (placed in a beaker of water) so as to allow monitoring of the reaction] and continued for 40 min (19 ml. collected). The reaction was 1/3 completed in 10 min. Most of the sulfolane (12.5 ml) was then removed by distillation in vacuo. The residue was triturated with methylene chloride (200 ml) and the off-white powder collected by filtration (250 mg, mp 220°–235°C) (the over-all appearance of the uv spectrum of this powder was the same as that of pure 4-amino-1-(beta-D-ribofuranosyl)-pyrazolo[3,4-d]pyrimidine. The solid was dissolved in water (40 ml), treated with purified charcoal (0.3 g) and then the solution was concentrated to 4 ml. by heating. The pure product which separated from solution as small white needles, 170 mg (60%), mp 247.5°–249°C (dec., darkens at 225°C). An additional 20 mg (7.7%) or product was obtained by concentrating the filtrate. The uv and nmr spectra of this material were identical to those of an authentic sample of 4-amino-1-(beta-D-ribofuranosyl)pyrazolo[3,4-d]pyrimidine.

The invention may be embodied in other specifc forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. Compounds of the formula:

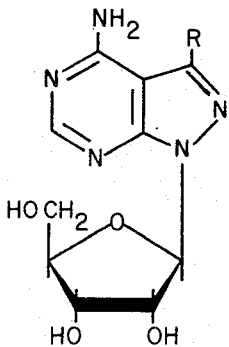

in which R is selected from the group consisting of carboxamidine, carboxylic acid, carboxamide, methyl formimidate, thiocarboxamide, carboxamidoxime, carboxamidrazone, and cyano.

2. The compound of the structure:

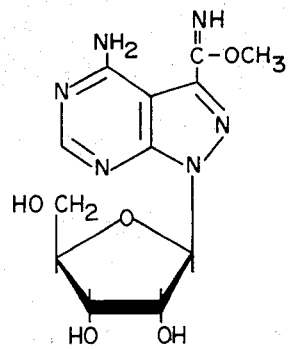

3. The compound of the structure:

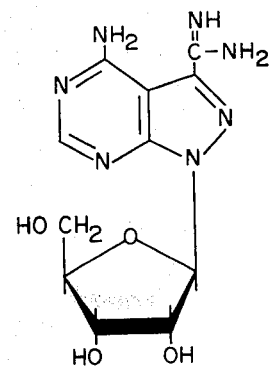

4. The compound of the structure:

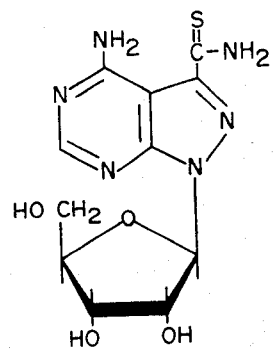

5. The compound of the structure:

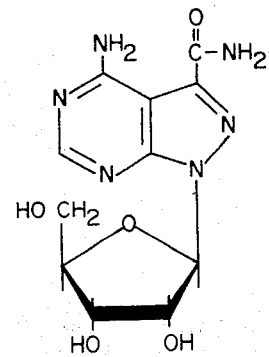

6. The compound of the structure:
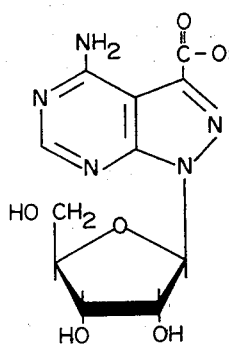
7. The compound of the structure:
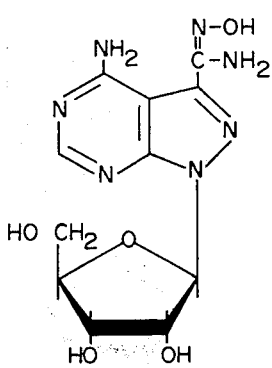
8. The compound of the structure:
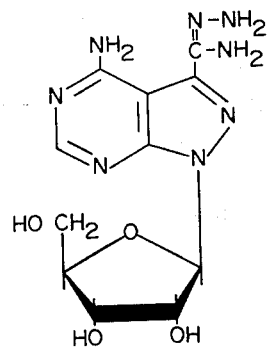
9. The compound of the structure:
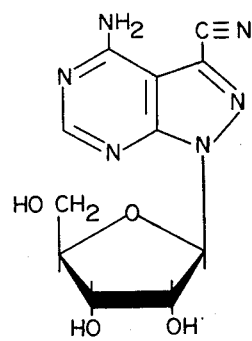
* * * * *

UNITED STATES PATENT OFFICE
CERTIFICATE OF CORRECTION

PATENT NO. : 3,962,211
DATED : June 8, 1976
INVENTOR(S) : LEROY B. TOWNSEND and ROBERT A. EARL It is certified that error appears in the above-identified patent and that said Letters Patent are hereby corrected as shown below:

Column 9, line 68, "9°C" should be --0°C--.

Signed and Sealed this

Twenty-fourth Day of August 1976

[SEAL]

Attest:

RUTH C. MASON
Attesting Officer

C. MARSHALL DANN
Commissioner of Patents and Trademarks